(12) United States Patent
Dong et al.

(10) Patent No.: US 7,655,808 B2
(45) Date of Patent: Feb. 2, 2010

(54) LEPTOMYCIN COMPOUNDS

(75) Inventors: Steven D. Dong, San Francisco, CA (US); Daniel V. Santi, San Francisco, CA (US); David C. Myles, Kensington, CA (US); Brian Hearn, San Francisco, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/241,218

(22) Filed: Sep. 30, 2008

(65) Prior Publication Data

US 2009/0042837 A1 Feb. 12, 2009

Related U.S. Application Data

(62) Division of application No. 11/142,482, filed on Jun. 1, 2005, now Pat. No. 7,446,196.

(60) Provisional application No. 60/577,253, filed on Jun. 3, 2004, provisional application No. 60/609,981, filed on Sep. 14, 2004.

(51) Int. Cl.
  C07D 413/00 (2006.01)
  C07D 309/30 (2006.01)
(52) U.S. Cl. ........................ 549/293; 544/149
(58) Field of Classification Search ............... 544/149; 549/293
  See application file for complete search history.

(56) References Cited

U.S. PATENT DOCUMENTS

| 4,725,621 A | 2/1988 | Bunge |
| 4,771,070 A | 9/1988 | Hokanson |
| 4,792,522 A | 12/1988 | Nettleton |
| 5,510,118 A | 4/1996 | Bosch |
| 5,534,270 A | 7/1996 | De Castro |
| 5,662,883 A | 9/1997 | Bagchi |
| 7,446,196 B2 * | 11/2008 | Dong et al. ............... 544/149 |
| 2003/0162740 A1 | 8/2003 | Wang |

FOREIGN PATENT DOCUMENTS

| WO | WO 81/01145 A1 | 4/1981 |
| WO | WO 2004/000212 A2 | 1/2005 |

OTHER PUBLICATIONS

U.S. Appl. No. 10/856,703, filed May 27, 2004, Johnson, Jr.
Carl et al., *J. Med. Chem.* 1981, 24(3), 479-480, "A Novel Connector Linkage Applicable in Prodrug Design".
Chemical Abstracts No. 105:102629 (abstract of JP 61-109717 A2 (1986)).
Doherty et al., *J. Nat. Cancer Inst.* 2003, 95(24), 1859-1868, "Cell Cycle Checkpoint Function in Bladder Cancer".
Fukuda et al, *Nature* 1997, 390, 308-311, "CRM1 is responsible for intracellular transport mediated by the nuclear export signal".

Hamamoto et al., *J. Antibiotics* 1983, 36 (6), 639-645, "Leptomycins A and B, New Antifungal Antibiotics I. Taxonomy of the Producing Strain and Their Fermentation, Purification and Characterization".
Hayakawa et al., *J. Antibiotics* 1987, 40(9), 1349-1352, "New Antitumor Antibiotics, Anguinomycins A and B".
Inoue et al., *J. Biol. Chem.* 2002, 277 (17), 15053-15060, "Nuclear Import and Export Signals in Control of the p53-related Protein p73".
Kobayashi et al., Ensho, Saisei 2004, 24(5), 578-583, "Role of matrix metalloproteinase-9 expression on cutaneous inflammation: possible treatment by leptomycin B application" (abstract).
Komiyama et al., *J. Antibiotics* 1985, 38 (2), 220-223, "Structural Study of a New Antitumor Antibiotic, Kazusamycin".
Komiyama et al., *J. Antibiotics* 1985, 38(2), 224-229, "Antitumor Activity of a New Antibiotic, Kazusamycin".
Komiyama et al., *J. Antibiotics* 1985, 38 (3), 427-429, "Antitumor activity of leptomycin B".
Kudo et al., *Exp. Cell Res.* 1998, 242, 540-547, "Leptomycin B Inhibition of Signal Mediated Nuclear Export by Direct Binding to CRM1".
Kudo et al., *Proc. Nat'l Acad. Sci.* (USA) 1999, 96(3), 9112-9117, "Leptomycin B Inactivates CRM1/exportin 1 by covalent modification at a cysteine residue in the central conserved region".
Kuhnt et al., *Applied Environ. Microbiol.* 1998, 64 (2), 714-720, "Microbial Conversion Products of Leptomycin B".
Lane et al., *Proc. Nat'l Acad. Sci.* (USA) 2000, 97, 8501-8506, "Activation of p53 in cervical carcinoma cells by small molecules".
Marabese et al., *Nucleic Acids Res.* 2003 31 (22), 6624-6632, "DNA damage induces transcriptional activation of p73 by removing C-EBPα repression on E2F1".

(Continued)

*Primary Examiner*—D. Margaret Seaman
*Assistant Examiner*—Nizal S Chandrakumar
(74) *Attorney, Agent, or Firm*—Laurelee A. Duncan

(57) ABSTRACT

Leptomycin-type compounds according to formula I

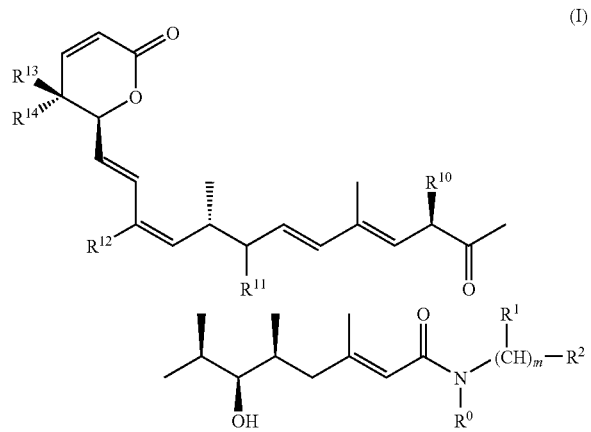

wherein $R^0$, $R^1$, $R^2$, $R^{10}$, $R^{11}$, $R^{12}$, $R^{13}$, $R^{14}$, and m are as defined herein, exhibit anti-tumor activity.

19 Claims, No Drawings

OTHER PUBLICATIONS

Meissner et al., *FEBS Letters* 2004, 576(1-2), 27-30, "Ratjadone and leptomycin B block CRM1-dependent nuclear export by identical mechanisms" (abstract).

Nishi et al., *J. Biol. Chem.* 1994, 269(9), 6320-6324, "Leptomycin B Targets a Regulatory Cascade of crm1, a Fission Yeast Nuclear Protein, Involved in Control of Higher Order Chromosome Structure and Gene Expression".

Peehl et al., *Prostate* 2003, 54, 258-267, "Leptomycin B Stabilizes and Activates p53 in Primary Prostatic Epithelial Cells and Induces Apoptosis in the LNCaP Cell Line".

University of Dundee, Dept. Surgery & Molecular Oncology, Lain Group Website, http://www.dundee.ac.uk/surgery/Non-Genotoxic. htm, accessed Dec. 6, 2004, "Non-genotoxic activation of the p53 tumor suppressor function".

Vigneri et al., *Nature Medicine* 2001, 7, 228-234, "Induction of apoptosis in chronic myelogenous leukemia cells through nuclear entrapment of BCR-ABL tyrosine kinase".

Vousden et al., *Nat. Rev. Cancer* 2002, 2, 594-504, "Live or Let Die: the Cell's Response to p53".

Yokomizo et al., *Oncogene* 1999 18 (8), 1629-1633, "Overexpression of the wild type p73 gene in human bladder cancer" (abstract).

Kuhnt, Michaela et al., "Microbial Conversion Products of Leptomycin B", Applied and Environmental Microbiology (Feb. 1998), p. 714-720.

* cited by examiner

LEPTOMYCIN COMPOUNDS

CROSS-REFERENCE TO RELATED APPLICATIONS

This application claims the benefit under 35 U.S.C. §119 (e) of U.S. Provisional Applications Nos. 60/577,253, filed Jun. 3, 2004, and 60/609,981, filed Sep. 14, 2004, the disclosures of which are incorporated herein by reference.

BACKGROUND OF THE INVENTION

1. Field of the Invention

This invention relates to leptomycin compounds and methods for making and using them.

2. Description of Related Art

Leptomycin B ("LMB") is an anti-tumor, anti-microbial natural product originally isolated from *Steptomyces* spp., as reported in Hokanson et al., U.S. Pat. No. 4,771,070 (1988) and Nettleton et al., U.S. Pat. No. 4,792,522 (1988).

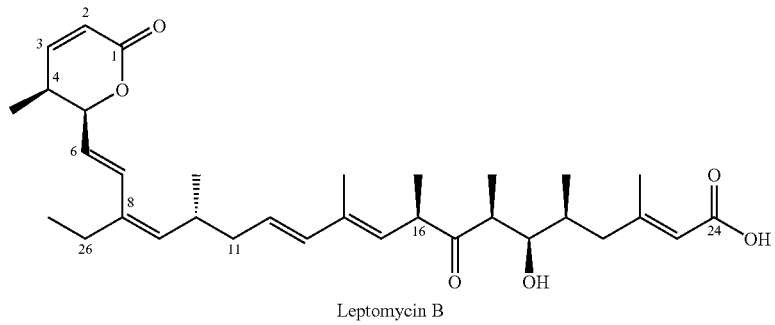

Leptomycin B

LMB is the archetype of a natural product family referred to as the leptomycin family, characterized by a 2,3-dehydro-δ-valerolactone ring at one end of the molecule ($C_1$-$C_5$) and an extended carbon chain having a 6E,8Z and a 12E,14E diene system located off $C_5$. A nitromethyl valerolactone LMB analog has been found to be inactive, whereas biotinylated LMB has been found to be active, suggesting that the 2,3-dehydro-δ-valerolactone structure is a crucial pharmacophore. Kudo et al., *Exp. Cell Res.* 1998, 242, 540-547.

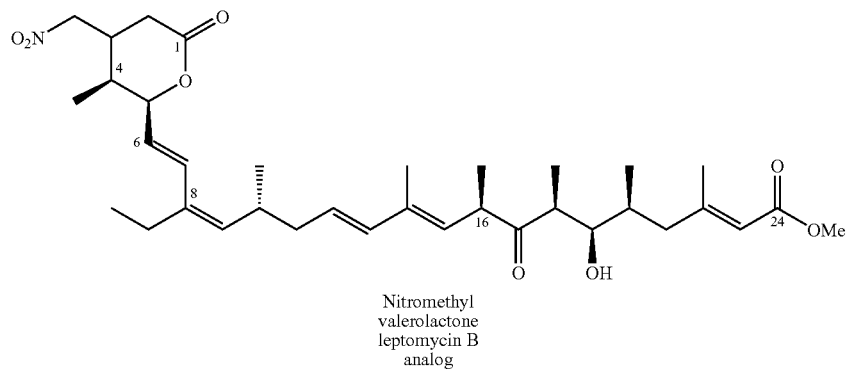

Nitromethyl
valerolactone
leptomycin B
analog

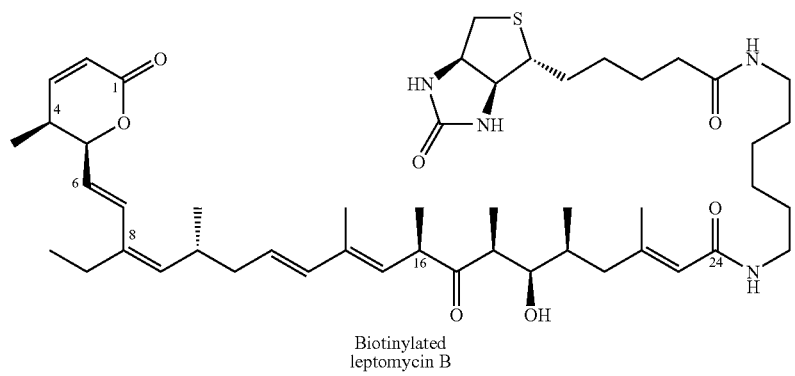

Biotinylated
leptomycin B

Other members of the leptomycin family include leptomycin A, ratjadone, anguinomycins A-D, callystatin A, kazusamycin A (also known as CL-1957B), kazusamycin B (also known as CL-1957E), leptolstatin, and leptofuranins A-D. The formulae of the other family members most structurally similar to leptomycin B are shown:

toxic, LMB was subjected to a bioconversion screening with a number of bacteria and fungi, from which a number of derivatives were isolated (Kuhnt et al., *Applied Environ. Microbiol.* 1998, 64 (2), 714-720): 26-hydroxyleptomycin B, 4,11-dihydroxyleptomycin B, 2,3-dihydroleptomycin B, and leptomycin B glutaminamide.

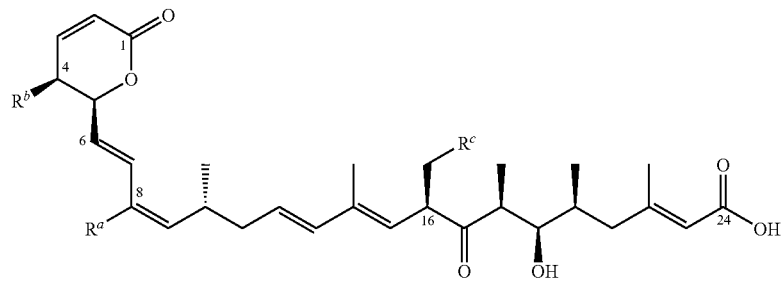

Leptomycin A: $R^a = CH_3$ $R^b = CH_3$ $R^c = H$
Anguinomycin A: $R^a = CH_3$ $R^b = H$ $R^c = H$
Anguinomycin B: $R^a = CH_2CH_3$ $R^b = H$ $R^c = H$
Kasuzamycin A: $R^a = CH_2CH_3$ $R^b = CH_3$ $R^c = OH$
Kasuzamycin B: $R^a = CH_3$ $R^b = CH_3$ $R^c = OH$ Although originally identified as a result of screening for antimicrobial activity, current interest in LMB resides prima-

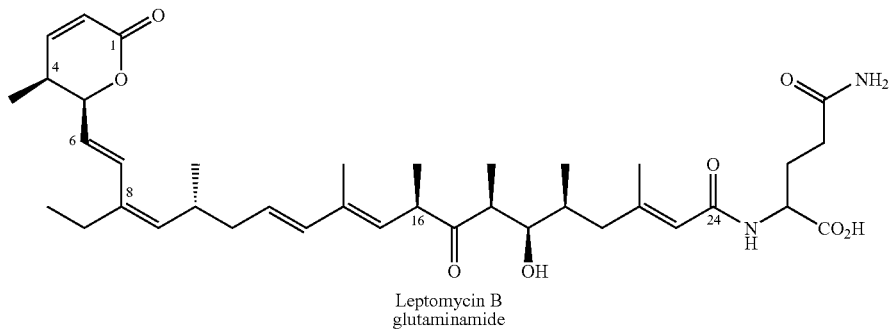

Leptomycin B glutaminamide rily in its potential as an anti-tumor agent. See, e.g. Komiyama et al., *J. Antibiotics* 1985, 38 (3), 427-429; Wang et al., US 2003/0162740 A1 (2003). At the cellular level, LMB acts by arresting cells at the end of the G1 and G2 phases of the cell cycle. At the molecular level, LMB acts as an inhibitor of the nuclear export receptor CRM1, which binds to and affects the nuclear translocation of "cargo proteins" such as P53, P73, STAT1, (i) ADAR1, Rev, actin, and Bcr-abl. Nishi et al., *J. Biol. Chem.* 1994, 269 (9), 6320-6324; Fukuda et al., *Nature* 1997, 390, 308-311; Kudo et al., cited supra.

However, LMB exhibits remarkable cytotoxicity towards mammalian cells (Hamamoto et al., *J. Antibiotics* 1983, 36 (6), 639-645), tempering its attractiveness as an anti-cancer agent. Thus, a phase 1 trial of LMB was halted in 1994 due to extreme toxicity. In an effort to identify more promising anti-cancer agents that exhibit LMB-like activity but are less This approach suffers from several drawbacks. The structural diversity in the products obtained was poor: the types of functional groups introduced were limited and the positions into which they were introduced were haphazard, precluding the systematic derivation of a structure-activity relationship. The number of compounds obtained in return for the effort expended was small (four compounds from a screening involving a total of 101 bacterial and fungal strains). The bioconversion yields were often low. Thus, an alternative approach to obtaining leptomycin compounds for use as an anti-cancer agent is desirable.

BRIEF SUMMARY OF THE INVENTION

In a first aspect, this invention provides a compound having a structure according to formula I

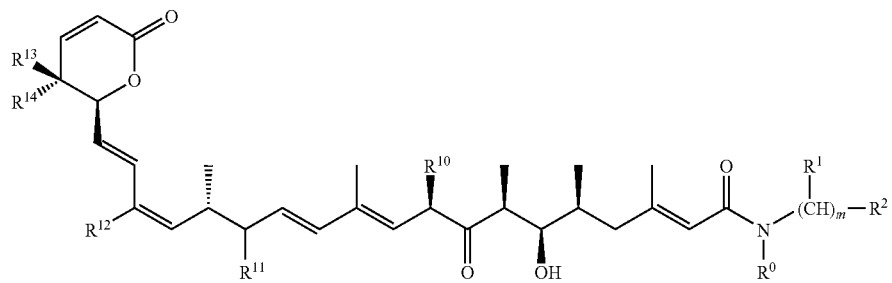

(I)

and the pharmaceutically acceptable esters, salts, solvates, hydrates and prodrug forms thereof, wherein m is 0, 1, 2, 3, 4, or 5;

$R^0$ is H, $C_1$-$C_5$ alkyl, $C_2$-$C_5$ alkenyl, or $C_2$-$C_5$ alkynyl;

each $R^1$ is independently H, $C_1$-$C_5$ alkyl, $C_2$-$C_5$ alkenyl, or $C_2$-$C_5$ alkynyl;

$R^2$ is H, aryl, cycloalkyl, a heterocyclic moiety,

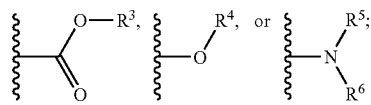

wherein $R^3$ is H, $C_1$-$C_5$ alkyl, $C_2$-$C_5$ alkenyl, or $C_2$-$C_5$ alkynyl, provided that $R^3$ is not H when m is 0;

$R^4$ is H, $C_1$-$C_5$ alkyl, $C_2$-$C_5$ alkenyl, $C_2$-$C_5$ alkynyl, aryl, cycloalkyl, or a heterocyclic moiety;

$R^5$ is H, $C_1$-$C_5$ alkyl, $C_2$-$C_5$ alkenyl, $C_2$-$C_5$ alkynyl, aryl, cycloalkyl, a heterocyclic moiety, or C(=O)O($C_1$-$C_5$ alkyl); and $R^6$ is H, $C_1$-$C_5$ alkyl, $C_2$-$C_5$ alkenyl, $C_2$-$C_5$ alkynyl, cycloalkyl or a fluorescent moiety; or $R^5$ and $R^6$ and the nitrogen to which they are commonly bonded combine to form a 4, 5, 6, or 7 membered nitrogen-containing heterocyclic ring structure;

$R^{10}$ is $CH_3$ or $CH_2OH$;

$R^{11}$ is H or OH;

$R^{12}$ is $CH_3$, $CH_2CH_3$; or $CH(OH)CH_3$; and one of $R^{13}$ and $R^{14}$ is H or $CH_3$ and the other is H or OH.

In a second embodiment, there is provided a method of inhibiting the proliferation of a target cell, comprising contacting the target cell with an effective amount of a compound of this invention. The target cell can be a cancer cell, especially a human breast cancer, lung cancer, ovarian cancer, prostate cancer, or leukemia cell. Also, the target cell can be a human papilloma virus (HPV)-associated cervical cancer cell or a bladder cancer cell.

In a third embodiment, there is provided a method of treating a hyperproliferative disease, comprising administering to a patient suffering from such hyperproliferative disease a therapeutically effective amount of a compound of this invention. The hyperproliferative disease so treated may be cancer, especially breast cancer, lung cancer, ovarian cancer, prostate cancer, or leukemia. Also, the hyperproliferative disease can be HPV-associated cervical cancer or bladder cancer. The patient preferably is a mammal, especially a human.

In a fourth embodiment, there is provided the use of a compound of this invention for the preparation of a medicament for treating a hyperproliferative disease, which can be cancer, especially breast cancer, lung cancer, ovarian cancer, prostate cancer, or leukemia. Also, the cancer can be HPV-associated cervical cancer or bladder cancer.

In a fifth embodiment, there is provided a pharmaceutical formulation comprising a compound of this invention and an excipient.

In a sixth embodiment, there is provided a method of inhibiting the export of a protein from the nucleus of a cell via a CRM1-mediated process, comprising contacting said cell with an inhibitory amount of a compound according to this invention.

In a seventh embodiment, there is provided a method of treating bladder cancer, comprising administering to a patient suffering from bladder cancer a therapeutically effective amount of leptomycin B.

DETAILED DESCRIPTION OF THE INVENTION

Definitions

"Alkyl" means an optionally substituted straight or branched chain hydrocarbon moiety having the specified number of carbon atoms in its longest chain portion (e.g., as in "$C_3$ alkyl," "$C_1$-$C_5$ alkyl," or "$C_1$ to $C_5$ alkyl," the latter two phrases referring to an alkyl group having from 1 to 5 carbon atoms in the longest chain portion) or, where the number of carbon atoms is not specified, from 1 to 4 carbon atoms in the longest chain portion.

"Alkenyl" means an optionally substituted straight or branched chain hydrocarbon moiety having at least one carbon-carbon double bond and the specified number of carbon atoms in its longest chain portion (e.g., as in "$C_3$ alkenyl," "$C_2$-$C_5$ alkenyl," or "$C_2$ to $C_5$ alkenyl," the latter two phrases referring to an alkenyl group having from 2 to 5 carbon atoms in the longest chain portion) or, where the number of carbon atoms is not specified, from 2 to 4 carbon atoms in the longest chain portion.

"Alkynyl" means an optionally substituted straight or branched chain hydrocarbon moiety having at least one carbon-carbon triple bond and the specified number of carbon atoms in its longest chain portion (e.g., as in "$C_3$ alkenyl," "$C_2$-$C_5$ alkynyl," or "$C_2$ to $C_5$ alkynyl," the latter two phrases referring to an alkynyl group having from 2 to 5 carbon atoms in the longest chain portion) or, where the number of carbon atoms is not specified, from 2 to 4 carbon atoms in the longest chain portion.

"Aryl" means an optionally substituted aromatic monocyclic, fused bicyclic, or fused polycyclic hydrocarbon or heterocyclic group having 1 to 20 carbon atoms in the ring portion(s), such as phenyl, naphthyl, pyrrolyl, indolyl, pyrazolyl, pyrazolinyl, imidazolyl, oxazolyl, isoxazolyl, thiazolyl, thiadazolyl, isothiazolyl, furyl, thienyl, oxadiazolyl, pyridinyl, N-oxo-pyridyl, pyrazinyl, pyrimidinyl, pyridazinyl, tetrazinyl, triazinyl, triazolyl, benzothiazolyl, benzoxazolyl, benzothienyl, quinolinyl, quinolinyl-N-oxide, isoquinolinyl, benzimidazolyl, benzofuryl, chromonyl, coumarinyl, cinnolinyl, quinoxalinyl, indazolyl, benzisothiazolyl, benzisoxazolyl, benzodiazinyl, tetrazolyl, benzofurazanyl, benzothiopyranyl, benzpyrazolyl, indolinyl, isochromanyl, isoindolinyl, naphthyridinyl, phthalazinyl, purinyl, quinazolinyl, and the like.

"Cycloalkyl" means an optionally substituted, saturated or unsaturated, non-aromatic cyclic hydrocarbon ring system, preferably containing 1 to 3 rings and 3 to 7 carbons per ring which may be further fused with a saturated or unsaturated $C_3$-$C_7$ carbocyclic ring. Exemplary cycloalkyl ring systems include cyclopropyl, cyclobutyl, cyclopentyl, cyclohexyl, cycloheptyl, cyclooctyl, cyclodecyl, cyclododecyl, and adamantyl.

"Arylalkyl" means an alkyl moiety substituted with an aryl moiety, with the open (unsatisfied) valence at the alkyl moiety, for example as in benzyl, phenethyl, N-imidazoylethyl, N-morpholinoethyl, ethylpyridinyl, and the like.

"Heterocycle", "heterocyclic," or "heterocyclo" means an optionally substituted, fully saturated or unsaturated, aromatic or nonaromatic ring system, for example, which is a 4 to 7 membered monocyclic, 7 to 11 membered bicyclic, or 10 to 15 membered tricyclic ring system, which has at least one heteroatom in at least one carbon atom-containing ring. "Heteroaryl" means a heterocycle in which the ring system is aryl. Each ring of the heterocyclic group containing a heteroatom may have 1, 2 or 3 heteroatoms selected from N, O and S, where the N and S optionally may be oxidized and the N optionally may be quarternized. Exemplary monocyclic heterocyclic ring systems include pyrrolidinyl, pyrrolyl, biotinyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thizaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridinyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, tetrazolyl, triazinyl, and triazolyl, and the like. Preferred heterocyclo groups include pyridinyl, morpholinyl, pyrazinyl, pyrimidinyl, pyrroyl, pyrazolyl, imidazolyl, thiazolyl, oxazolyl, isoxazolyl, thiadiazolyl, oxadiazolyl, thienyl, furanyl, quinolinyl, isoquinolinyl, piperazinyl, and piperidinyl.

Where it is indicated that a group may be substituted, for example by use of "substituted or unsubstituted" or "optionally substituted" phrasing, such group may have one or more independently selected substituents, preferably one to five in number, more preferably one or two in number. It is understood that substituents and substitution patterns can be selected by one of ordinary skill in the art to provide compounds that are chemically stable and that can be synthesized by techniques known in the art as well as the methods set forth herein. Examples of suitable substituents include alkyl, alkenyl, alkynyl, aryl, halo, trifluoromethoxy, trifluoromethyl, hydroxy, alkoxy, cycloalkyloxy, heterocyclooxy, alkanoyl, alkanoyloxy, amino, alkylamino quarternary ammonium, aralkylamino, heterocycloalkyl, cycloalkylamino, heterocyloamino, dialkylamino, alkanoylamino, thio, alkylthio, cycloalkylthio, heterocyclothio, ureido, nitro, cyano, carboxy, caroboxylalkyl, carbamyl, alkoxycarbonyl, alkylthiono, arylthiono, alkylsulfonyl, sulfonamindo, aryloxy, and the like, in addition to those specified herein. Preferably, the substituent(s) for alkyl, alkenyl, and alkynyl moieties are from one to three in number and are independently selected from N-pyrrolidinyl, N-morpholinyl, N-azetidinyl, hydroxyl, halo, alkoxyl, cyano, amino, alkylamino, and dialkylamino. Preferably, the substituent(s) for aryl, cycloalkyl, and heterocycloalkyl moieties are from one to three in number and are independently selected from alkyl, alkenyl, alkynyl, hydroxyalkyl, haloalkyl, hydroxyl, halo, alkoxyl, cyano, aminoalkyl, alkylaminoalkyl, dialkylaminoalkyl, amino, alkylamino, and dialkylamino.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates are also encompassed within the scope of this invention.

"Pharmaceutically acceptable ester" means an ester that hydrolyzes in vivo (for example in the human body) to produce the parent compound or a salt thereof or has per se activity similar to that of the parent compound. Suitable ester groups include, without limitation, those derived from pharmaceutically acceptable aliphatic carboxylic acids, particularly alkanoic, alkenoic, cycloalkanoic and alkanedioic acids, in which each alkyl or alkenyl moiety preferably has no more than six carbon atoms. Illustrative esters include formates, acetates, propionates, butyrates, acrylates, citrates, succinates, and ethylsuccinates.

"Pharmaceutically acceptable salts" means salts of the active compounds that are prepared with relatively nontoxic acids or bases, depending on the particular substituents found on the compounds described herein. When a compound contains a relatively acidic functionality, a base addition salt can be obtained by contacting the neutral form of such compound with a sufficient amount of the desired base, either neat or in a suitable inert solvent. Examples of pharmaceutically acceptable base addition salts include sodium, potassium, calcium, ammonium, organic amino, or magnesium salt, or a similar salt. When a compound contains a relatively basic functionality, an acid addition salt can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohy-drogen-sulfuric, hydriodic, or phosphorous acids and the like, as well as the salts derived from relatively nontoxic organic acids like acetic, ascorbic, propionic, isobutyric, maleic, malonic, lactic, malic, glutamic, benzoic, succinic, suberic, fumaric, mandelic, phthalic, benzenesulfonic, p-tolylsulfonic, citric, tartaric, methanesulfonic, lactobionic, and the like. Also included are salts of amino acids such as arginate and the like, and salts of organic acids like glucuronic or galactunoric acids and the like. Where a compound contains both basic and acidic functionalities, they can be converted into either a base or an acid addition salt.

The present invention includes within its scope prodrugs of the compounds of this invention. Such prodrugs are in general functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in Wermuth, "Designing Prodrugs and Bioprecursors," in Wermuth, ed., *The Practice of Medicinal Chemistry*, 2nd Ed., pp. 561-586 (Academic Press 2003), the disclosure of which is incorporated herein by reference. Prodrugs include esters that hydrolyze in vivo (for example in the human body) to produce a compound of this invention or a salt thereof. Suitable ester groups include, without limitation, those derived from pharmaceutically acceptable aliphatic carboxylic acids, particularly alkanoic, alkenoic, cycloalkanoic and alkanedioic acids, in which each alkyl or alkenyl moiety preferably has no more than six carbon atoms. Illustrative esters include but are not limited to formates, acetates, propionates, butyrates, acrylates, citrates, succinates, and ethylsuccinates.

"Therapeutically effective amount" means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Where a range is stated, as in "$C_1$ to $C_5$ alkyl" or "5 to 10%," such range includes the end points of the range.

Compounds and Methods

Referring back to formula I, in a preferred embodiment $R^0$ is H, $R^{10}$ is $CH_3$, $R^{11}$ is H, $R^{12}$ is $CH_3$, $R^{13}$ is $CH_3$, and $R^{14}$ is H, while $R^1$, $R^2$, and m retain the meanings assigned in the BRIEF SUMMARY OF THE INVENTION section above.

In another preferred embodiment $R^0$ is H, $R^{10}$ is $CH_3$, $R^{11}$ is H, $R^{12}$ is $CH_3$ or $CH_2CH_3$, $R^{13}$ is H, and $R^{14}$ is H, while $R^1$, $R^2$, and m retain the meanings assigned in the BRIEF SUMMARY OF THE INVENTION section above.

In yet another preferred embodiment $R^0$ is H, $R^{10}$ is $CH_2OH$, $R^{11}$ is H, $R^{12}$ is $CH_3$ or $CH_2CH_3$, $R^{13}$ is $CH_3$, and $R^{14}$ is H, while $R^1$, $R^2$, and m retain the meanings assigned in the BRIEF SUMMARY OF THE INVENTION section above.

In an especially preferred embodiment of the invention, $R^0$ is H, $R^{10}$ is $CH_3$, $R^{11}$ is H, $R^{12}$ is $CH_2CH_3$, $R^{13}$ is $CH_3$, and $R^{14}$ is H, corresponding to a compound having a structure according to formula Ia. ($R^1$, $R^2$ and m retain the meanings assigned in the BRIEF SUMMARY OF THE INVENTION section above.)

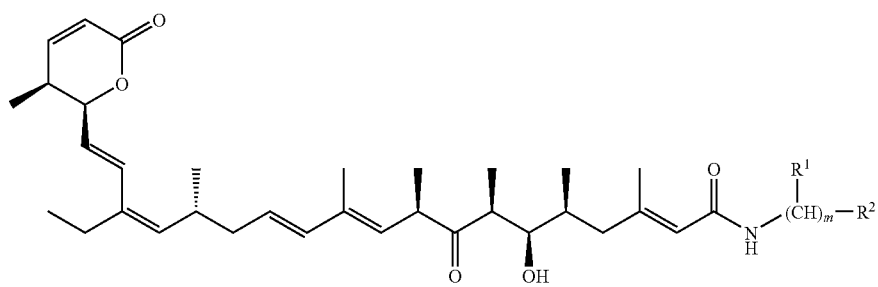

(Ia)

Where $R^2$ is a heterocyclic moiety, it preferably is

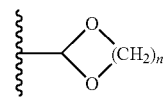

where n is 2, 3, or 4.

In a preferred embodiment, $R^3$ is other than H.

Exemplary $R^6$ fluorescent moieties include

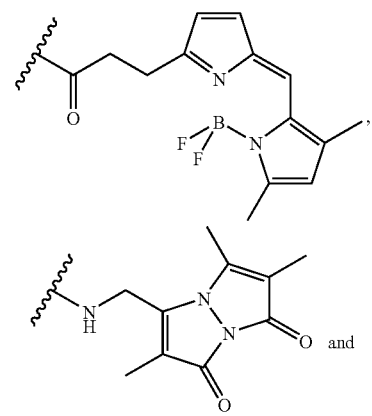

and

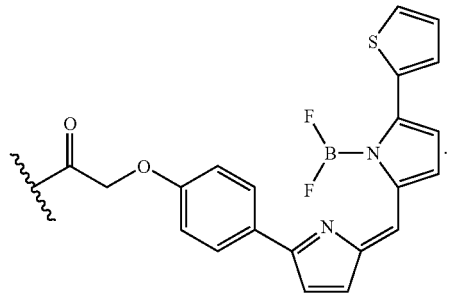

Synthons for the attachment of these and other fluorescent moieties to LMB are available from Molecular Probes, Eugene, Oreg., USA. Fluoresecent probe bearing LMB compounds, aside from unexpectedly having cytotoxic activity, can be used as biomarkers for studying the mechanism of action and intracellular distribution of LMB compounds. However, in certain embodiments, $R^6$ preferably is other than a fluorescent moiety.

Illustrative examples of compounds according to formula Ia are given in Table 1.

TABLE 1-continued

Compounds

| Compound | |
|---|---|
| | 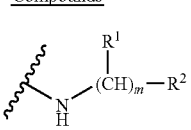 |
| 20 | 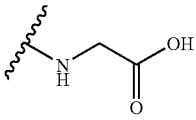 |
| 21 | |

Compounds of this invention can be used for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; treat ovarian cancer; small cell and non-small cell lung cancer; breast cancer sarcomas, such as fibrosarcoma, malignant fibrous histiocytoma, embryonal rhabdomysocarcoma, leiomysosarcoma, neurofibrosarcoma, osteosarcoma, synovial sarcoma, liposarcoma, and alveolar soft part sarcoma; neoplasms of the central nervous systems, particularly brain cancer; lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as: inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary. Especially, the cancer can be prostate cancer, human papilloma virus (HPV)-associated cervical cancer, leukemia (especially chronic myeloid leukemia or CML), and bladder cancer.

Non-cancer disorders that are characterized by cellular hyperproliferation can also be treated by compounds of this invention. Illustrative examples of such disorders include but are not limited to: atrophic gastritis, inflammatory hemolytic anemia, graft rejection, inflammatory neutropenia, bullous pemphigoid, coeliac disease, demyelinating neuropathies, dermatomyositis, inflammatory bowel disease (ulcerative colitis and Crohn's disease), multiple sclerosis, myocarditis, myositis, nasal polyps, chronic sinusitis, pemphigus vulgaris, primary glomerulonephritis, psoriasis, surgical adhesions, stenosis or restenosis, scleritis, scleroderma, eczema (including atopic dermatitis, irritant dermatitis, allergic dermatitis), periodontal disease (i.e., periodontitis), polycystic kidney disease, and type I diabetes. Other examples include vasculitis (e.g., Giant cell arteritis (temporal arteritis, Takayasu's arteritis), polyarteritis nodosa, allergic angiitis and granulomatosis (Churg-Strauss disease), polyangitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system, Wegener's granulomatosis, Kawasaki's disease, vasculitis of the central nervous system, Buerger's disease and systemic sclerosis); gastrointestinal tract diseases (e.g. pancreatitis, Crohn's disease, ulcerative colitis, ulcerative proctitis, primary sclerosing cholangitis, benign strictures of any cause including ideopathic (e.g., strictures of bile ducts, esophagus, duodenum, small bowel or colon); respiratory tract diseases (e.g., asthma, hypersensitivity pneumonitis, asbestosis, silicosis and other forms of pneumoconiosis, chronic bronchitis and chronic obstructive airway disease); nasolacrimal duct diseases (e.g., strictures of all causes including ideopathic); and eustachean tube diseases (e.g., strictures of all causes including ideopathic). Especially, the non-cancer condition can be plantar warts, cardiac hypertrophy, or cancer cachexia.

Compounds of this invention can be administered in combination with other anti-cancer or cytotoxic agents, including alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, microtubule stabilizers, nucleoside (purine or pyrimidine) analogs, nuclear export inhibitors, proteasome inhibitors, topoisomerase (I or II) inhibitors, tyrosine kinase inhibitors. Specific anti-cancer or cytotoxic agents include β-lapachone, ansamitocin P3, auristatin, bicalutamide, bleomycin, bleomycin, bortezomib, busulfan, calicheamycin, callistatin A, camptothecin, capecitabine, CC-1065, cisplatin, cryptophycins, daunorubicin, discodermolide, disorazole, docetaxel, doxorubicin, duocarmycin, dynemycin A, epothilones, etoposide, floxuridine, floxuridine, fludarabine, fluoruracil, gefitinib, geldanamycin, 17-allylamino-17-demethoxygeldanamycin (17-AAG), 17-(2-dimethylaminoethyl)amino 17-demethoxygeldanamycin (17-DMAG), gemcitabine, hydroxyurea, imatinib, interferons, interleukins, irinotecan, leptomycin B, maytansine, methotrexate, mitomycin C, oxaliplatin, paclitaxel, spongistatins, suberoylanilide hydroxamic acid (SAHA), thiotepa, topotecan, trichostatin A, vinblastine, vincristine, and vindesine.

Preferably, compounds of this invention are provided in a purified and isolated form, for example following column chromatography, high-pressure liquid chromatography, recrystallization, or other purification technique. Where particular stereoisomers of compounds of this invention are denoted, such stereoisomers preferably are substantially free of other stereoisomers.

Compounds of this invention may be used in a pharmaceutical formulation comprising a compound of this invention and an excipient. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science*

*and Practice of Pharmacy,* 20th Ed. (Lippincott Williams & Wilkins 2003), the disclosure of which is incorporated herein by reference.

The composition may be in any suitable form such as solid, semisolid, or liquid form. In general, the pharmaceutical preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semisolid, or liquified form. In addition, auxiliary stabilizing, thickening, and coloring agents and perfumes may be used. Preferred modes of administration include intravenously and, in the case of certain indications such a cervical cancer, bladder cancer, or plantar warts, topically.

Where applicable, compounds of this invention may be formulated as microcapsules and nanoparticles. General protocols are described for example, in Bosch et al., U.S. Pat. No. 5,510,118 (1996); De Castro, U.S. Pat. No. 5,534,270 (1996); and Bagchi et al., U.S. Pat. No. 5,662,883 (1997), which are all incorporated herein by reference. By increasing the ratio of surface area to volume, these formulations allow for the oral delivery of compounds that would not otherwise be amenable to oral delivery.

Dosage levels of the compounds of the present invention are of the order from about 0.1 mg to about 100 mg per kilogram of body weight per day, preferably from about 1 mg to about 50 mg per kilogram of body weight per day. More preferably, the dosage levels are from about 5 mg to about 20 mg per kilogram of body weight per day, corresponding to 350 mg to 1400 mg per patient per day, assuming a 70 kg patient. The compounds of the present invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain carrier material, which may vary from about 5 percent to about 95 percent of the total composition. Dosage unit forms will generally contain from about 5 mg to about 500 mg of active ingredient.

It will be understood, however, that the specific dose level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

Those skilled in the art will appreciate that compounds of this invention having a primary or secondary amine group, such as compounds 15-17, can be used in therapeutic conjugates comprising a targeting moiety, a linker moiety, and an active agent. In such a conjugate the leptomycin compound is the active agent, or warhead, that is delivered to a target cell by the action of the targeting moiety. The targeting moiety can be an antibody (especially a monoclonal antibody) that has affinity for a characteristic molecule on the target cell. By way of specific illustration, in cancer chemotherapy, the characteristic molecule can be a tumor-associated antigen recognized by the monoclonal antibody. The linker moiety is designed to cleave when the conjugate is internalized by the cancer cell or in proximity thereof, releasing the leptomycin compound as an anti-cancer drug. The primary or secondary amine serves as a convenient attachment point for the leptomycin compound to the linker moiety, in particular a "self-immolating" group such as a p-aminobenzyloxycarbonyl (PABC) group. See, e.g., Carl et al., *J. Med. Chem.* 1981, 24 (3), 479-480; and Carl et al., WO 81/01145 (1981); the disclosures of which are incorporated herein by reference.

Without being bound by theory, we believe that compounds of our invention function by a mechanism analogous to that of LMB to inhibit CRM-1 mediated nuclear export processes in the target cancer cells, thus inducing apoptosis. The 2,3-dehydro-δ-valerolactone moiety in LMB is a Michael reaction acceptor. LMB has been shown to inhibit CRM1 by forming a Michael adduct at this location with cysteine 529 of CRM1 (Kudo et al., *Proc. Nat'l Acad. Sci.* (*USA*) 1999, 96 (3), 9112-9117). The compounds of this invention retain the critical 2,3-dehydro-δ-valerolactone pharmacophore and therefore can be expected to function by the same inhibitory mechanism.

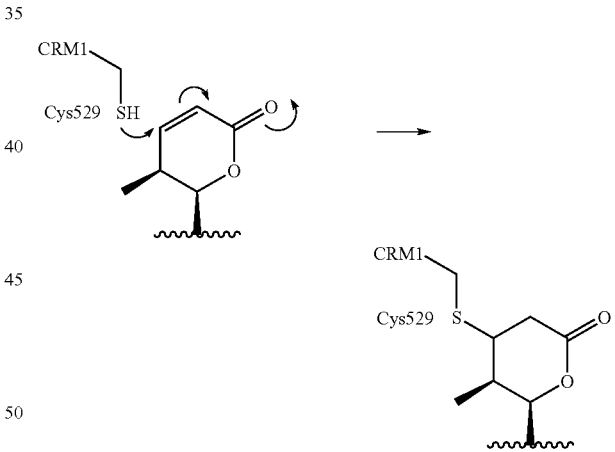

Many cancer cells have mutations resulting in the loss of function of the apoptosis-inducing, tumor suppressor protein p53. Vousden et al., *Nat. Rev. Cancer* 2002, 2, 594-504. Examples of such cancers include prostate cancer and human papilloma virus (HPV) associated cervical cancer. It has been shown that LMB causes the accumulation of p53 protein in the nucleus of cervical cancer cells. Lane et al., *Proc. Nat'l Acad. Sci.* (*USA*) 2000, 97, 8501-8506. In prostate cancers characterized by defective up-regulation of p53 due to DNA damage, the cell nucleus is deficient in p53. LMB has been shown to trap p53 in the nucleus and induce apopotosis. Hence, prostate cancer cells are highly sensitive to LMB. Peehl et al., *Prostate* 2003, 54, 258-267.

Against appropriate types of cancers, compounds of this invention can be used synergistically with other anticancer agents, in particular tyrosine kinase inhibitors such as imatinib (whose mesylate is known by the proprietary name Gleevec™). Some cancers such as chronic myelogenous leukemia (CML) are characterized by expression of the fusion protein Bcr-Abl. While normally Bcr-Abl is not imported into the nucleus, the Bcr-Abl/imatinib complex is imported into the nucleus. If LMB is also present, it prevents the export of Bcr-Abl out of the nucleus. Further, nuclear-entrapped Bcr-Abl induces apoptosis, resulting in the death of Bcr-Abl positive cells. See, e.g. Vigneri et al., *Nature Medicine* 2001, 7, 228-234; Wang et al., US 2003/0162740 A1 (2003). Thus, the combination of imatinib and an LMB compound of this invention can provide a mechanism for synergistically attacking Bcr-Abl positive cancer cells.

Thus, compounds of this invention can be used to inhibit the nuclear export of proteins such as p53, p73, Bcr-Abl, STAT1, (i) ADAR1, Rev, and actin from the nucleus of a cell, by forming a covalent adduct with CRM1 and interfering with the CRM1 mediated export process for such proteins. In one embodiment, the inhibited protein is p53. In another embodiment, the inhibited protein is Bcr-Abl. While a certain variability is to be expected depending on the cell type and the target protein, generally the inhibitory amount used will be in the range of 0.3 to 740 nM, preferably 0.3 to 20 nM, more preferably 0.3 to 2.0 nM.

The practice of this invention can be further understood by reference to the following examples, which are provided by way of illustration and not of limitation.

EXAMPLE 1

General Procedure for Solution-Phase Synthesis

Compounds of this invention can be synthesized by a solution phase method, per the equation below, using LMB as the archetype.

LMB was obtained by fermentation of *Streptomyces* sp. ATCC 39366 from the American Type Culture Collection (Manassas, Va.). Screening of single isolates from the specimen as received from ATCC yielded a high producing isolate, which was used for the fermentation. LMB is also available commercially from Sigma-Aldrich (St. Louis, Mo.).

LMB (12.2 mg, 0.027 mmol, 1 eq), N-hydroxybenzotriazole ("HOBt," 3.4 mg, 0.025 mmol, 1.1 eq), and (benzotriazol-1-yloxy)tripyrrolidinophosphonium hexafluorophosphate ("PyBOP," 13 mg, 0.025 mmol, 1.1 eq) were dissolved in dry N,N-dimethylformamide ("DMF," 400 µL). Amine A (0.025 mmol, 1.1 eq) and diisopropylethylamine ("DIEA," also known as Hünig's base, 16 µL, 0.09 mmol, 4 eq) were subsequently added. The reaction was stirred at room temperature under nitrogen for 20 hours. The reaction was partitioned between water and dichloromethane ("DCM"). The organic layer was washed with water (2×), saturated sodium bicarbonate (1×), and brine (1×). The organic layer was dried over sodium sulfate, filtered, and concentrated in vacuo. The crude product (an oil) was applied to a silica flash column (0.5×5 cm) and eluted with either 0% to 60% acetone/hexane or 0% to 10% methanol/DCM. Fractions containing product Ia were pooled and concentrated in vacuo.

EXAMPLE 2

General Procedure for Solid-Phase Synthesis

Alternatively, solid-phase synthesis may be used to make compounds of this invention, as depicted in the following equation:

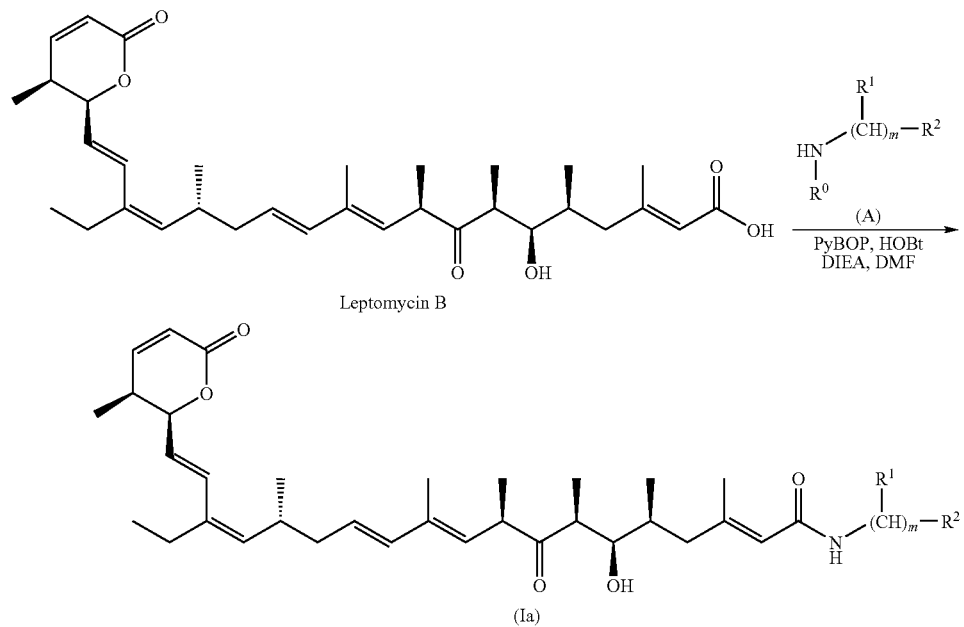

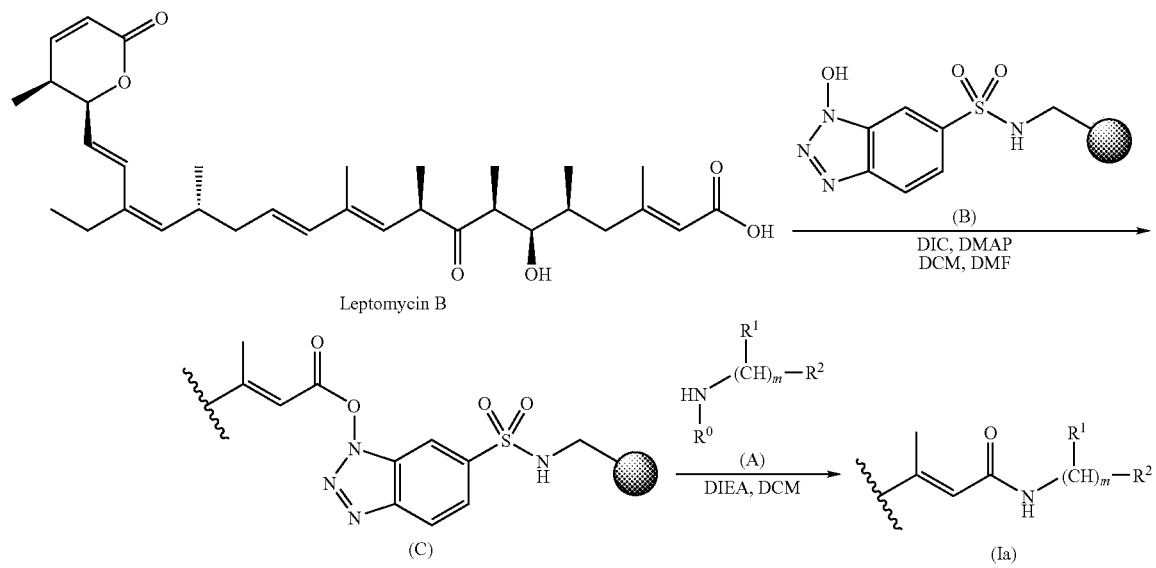

A 10 mL solid-phase reactor is charged with PS-HOBT (HL) resin (B, 267 mg., ~0.24 mmol, 1.0 eq, 0.9 mmol/g, Argonaut; the resin matrix is denoted by the black ball in the equation above) and a solution of 4-dimethylaminopyridine ("DMAP," 18 mg, 0.144 mmol. 0.6 eq) in DCM (3.2 mL). A solution of LMB (200 mg, 0.37 mmol, 1.53 eq) in dry DMF (960 µL) is added to the reaction mixture and agitated with nitrogen for 1 min. A solution of diisopropylcarbodiimide ("DIC," 170 µL, 1.06 mmol, 4.4 eq) in DCM is added to the reaction, and the reaction mixture is agitated on a shake table at room temperature for 3 hr. The solvent is removed by vacuum filtration. The resin is rinsed with DMF (3×), DCM (3×), DMF (3×), and tetrahydrofuran (3×) to afford LMB-charged resin C, which is recovered and stored at −20° C.

Amine A (0.036 mmol, 0.6 eq) and diisopropylethylamine (7 µL, 0.04 mmol, 0.67 eq) are dissolved in dry DCM (1 mL). LMB-charged resin C (110 mg, ~0.06 mmol, 1 eq) is suspended in the solution and stirred at room temperature for 3 hours. The solution is filtered, and the resin is rinsed with DCM (3×). The combined filtrates are concentrated in vacuo to yield a yellow oil. The crude oil is applied to a silica flash column (0.5×5 cm) and eluted with either 0% to 60% acetone/hexane or 0% to 10% methanol/DCM. Fractions containing product Ia are pooled and concentrated in vacuo.

EXAMPLE 3

Compound 1

Compound 1 was made following the procedure of Example 1 using methylamine (Sigma-Aldrich). LRMS calculated for $C_{34}H_{51}NO_5$: 553.4. found 554.4 (M+H).

EXAMPLE 4

Compound 2

Compound 2 was made following the procedure of Example 1 using 2-aminoethanol (Sigma-Aldrich). $^{13}C$ NMR (100 MHz, CDCl$_3$) δ 12.27, 13.02, 13.25, 13.52, 16.06, 17.94, 20.91, 26.45, 30.90, 32.22, 33.27, 33.48, 40.76, 42.27, 45.11, 45.59, 47.25, 62.47, 73.41, 81.59, 119.50, 119.85, 122.50, 128.06, 130.20, 135.04, 135.42, 136.37, 136.96, 151.83, 152.69, 164.58, 168.37, 215.39; HRMS calculated for $C_{35}H_{53}NO_6$: 583.39729. found 584.39423 (M+H).

EXAMPLE 5

Compound 3

Compound 3 was made following the procedure of Example 1 using 4-phenylbenzylamine (Sigma-Aldrich). $^{13}C$ NMR (100 MHz, CDCl$_3$) δ 12.27, 12.65, 13.00, 13.35, 13.67, 16.09, 18.04, 20.92, 26.49, 32.23, 33.30, 33.48, 40.77, 42.91, 45.00, 45.49, 46.92, 73.98, 81.48, 119.60, 119.92, 122.59, 126.99, 127.23, 127.31, 128.02, 128.23, 128.72, 130.16, 135.07, 135.46, 136.30, 136.91, 137.69, 151.56, 152.58, 164.35, 166.69, 215.25; LRMS calculated for $C_{46}H_{59}NO_5$: 705.4. found 707.0 (M+H).

EXAMPLE 6

Compound 4

Compound 4 was made following the procedure of Example 1 using 3-(2-aminoethyl)pyridine, available from Lancaster Synthesis. $^{13}C$ NMR (100 MHz, CDCl$_3$) δ 12.27, 12.99, 13.09, 13.52, 16.11, 17.96, 20.87, 26.46, 30.87, 32.19, 32.95, 33.30, 33.48, 40.06, 40.76, 44.96, 45.55, 47.20, 73.59, 81.48, 119.57, 119.90, 122.58, 123.54, 127.96, 128.15, 130.11, 134.78, 135.09, 135.42, 136.28, 136.54, 136.91, 147.52, 149.86, 151.64, 152.33, 164.37, 167.05, 215.20; LRMS calculated for $C_{40}H_{56}N_2O_5$: 644.9. found 646.0 (M+H).

EXAMPLE 7

Compound 5

Compound 5 was made following the procedure of Example 1 using 6-aminoindazole (Sigma-Aldrich). LRMS calculated for $C_{40}H_{53}N_3O_5$: 655.9. found 657.0 (M+H).

EXAMPLE 8

Compound 6

Compound 6 was made following the procedure of Example 1 using N-Boc-ethylenediamine (Sigma-Aldrich). $^{13}$C NMR (100 MHz, CDCl$_3$) δ 12.26; 12.87, 12.97, 13.51, 16.11, 17.84, 20.84, 26.30, 26.38, 26.45, 28.30, 32.15, 33.28, 33.48, 39.94, 40.50, 40.74, 45.05, 45.51, 45.60, 46.19, 46.23, 47.03, 73.82, 79.29, 81.46, 119.80, 119.91, 122.60, 127.91, 128.16, 130.08, 135.10, 135.40, 136.23, 136.89, 151.60, 151.96, 156.62, 164.34, 167.53, 215.24; LRMS calculated for $C_{40}H_{62}N_2O_7$: 682.5. found 683.6 (M+H).

EXAMPLE 9

Compound 7

Compound 7 was made following the procedure of Example 1 using N,N-dimethylethylenediamine (Sigma-Aldrich). $^{13}$C NMR (100 MHz, CDCl$_3$) δ 12.29, 12.68, 12.99, 13.53, 13.61, 16.09, 17.77, 20.81, 26.48, 32.13, 33.25, 33.49, 36.28, 40.75, 45.02, 45.52, 46.82, 57.90, 73.93, 81.43, 119.97, 122.66, 127.90, 128.17, 130.05, 135.15, 135.39, 136.27, 136.90, 151.49, 164.25, 166.92, 215.25; LRMS calculated for $C_{37}H_{58}N_2O_5$: 610.4. found 612.0 (M+H).

EXAMPLE 10

Compound 8

Compound 8 was made following the procedure of Example 1 using 4-(3-aminopropyl)morpholine (Sigma-Aldrich). $^{13}$C NMR (100 MHz, CDCl$_3$) δ 8.61, 12.28, 12.84, 12.99, 13.56, 16.11, 17.86, 20.84, 25.16, 26.47, 32.17, 33.22, 33.49, 38.17, 40.76, 45.03, 45.52, 46.01, 46.95, 53.43, 57.15, 66.61, 73.72, 81.46, 119.94, 120.03, 122.62, 127.94, 128.14, 130.09, 135.12, 135.42, 136.31, 136.90, 151.57, 215.27; LRMS calculated for $C_{40}H_{62}N_2O_6$: 666.5. found 667.5 (M+H).

EXAMPLE 11

Compound 9

Compound 9 was made following the procedure of Example 1 using 2-phenoxyethylamine (Sigma-Aldrich). $^{13}$C NMR (100 MHz, CDCl$_3$) δ 12.28, 12.65, 13.00, 13.54, 13.63, 16.08, 17.95, 20.87, 26.48, 32.19, 33.26, 33.48, 38.57, 40.76, 44.99, 45.51, 46.85, 66.75, 74.00, 81.45, 114.39, 119.60, 119.96, 121.00, 122.62, 127.98, 128.17, 129.47, 130.10, 135.09, 135.43, 136.30, 136.89, 151.53, 152.58, 158.46, 166.87, 215.20; LRMS calculated for $C_{41}H_{57}NO_6$: 659.4. found 661.0 (M+H).

EXAMPLE 12

Compound 10

Compound 10 was made following the procedure of Example 1 using glycine methyl ester, available from Novabiochem. $^{13}$C NMR (100 MHz, CDCl$_3$) δ 12.27, 12.77, 12.99, 13.52, 16.06, 18.00, 20.84, 26.47, 31.36, 32.16, 33.25, 33.47, 36.43, 40.74, 40.94, 45.06, 45.52, 46.90, 52.22, 73.91, 81.45, 118.95, 119.94, 122.62, 127.95, 128.14, 130.10, 135.09, 135.41, 136.30, 136.89, 151.56, 153.58, 162.49, 164.32, 166.74, 170.67, 215.16; LRMS calculated for $C_{36}H_{53}NO_7$: 611.4. found 613.0 (M+H).

EXAMPLE 13

Compound 11

Compound 11 was made following the procedure of Example 1 using 2-(2-aminoethyl)-1,3-dioxolane, available from TCI-America. $^{13}$C NMR (100 MHz, CDCl$_3$) δ 12.28, 12.65, 12.98, 13.52, 13.58, 16.07, 17.84, 20.82, 26.47, 32.14, 32.75, 33.24, 33.48, 34.27, 40.74, 44.95, 45.51, 46.81, 64.85, 74.02, 81.43, 103.67, 119.95, 120.08, 122.64, 127.93, 128.14, 130.06, 135.11, 135.41, 136.29, 136.88, 151.40, 151.52, 164.27, 166.68, 215.20; LRMS calculated for $C_{38}H_{57}NO_7$: 639.4. found 641.0 (M+H).

EXAMPLE 14

Compound 12

Compound 12 was made following the procedure of Example 1 using (R)-2-amino-3-benzyloxy-1-propanol (Sigma-Aldrich). $^{13}$C NMR (100 MHz, CDCl$_3$) δ 12.28, 12.84, 13.00, 13.57, 16.08, 17.88, 20.84, 26.48, 32.16, 33.25, 33.48, 40.76, 45.16, 45.52, 46.93, 50.56, 63.87, 70.30, 73.39, 73.81, 81.45, 119.62, 119.94, 122.63, 127.66, 127.84, 127.95, 128.16, 128.45, 130.08, 135.12, 135.41, 136.30, 136.90, 137.59, 151.56, 152.94, 164.34, 167.26, 215.21; LRMS calculated for $C_{43}H_{61}NO_7$: 703.4. found 705.0 (M+H).

EXAMPLE 15

Compound 13

Compound 13 was made following the procedure of Example 1 using D-alanine tert-butyl ester (Novabiochem). $^{13}$C NMR (100 MHz, CDCl$_3$) δ 12.28, 12.60, 13.00, 13.56, 16.07, 17.85, 18.79, 20.85, 26.48, 27.90, 32.18, 33.26, 33.48, 40.74, 45.08, 45.46, 46.80, 48.25, 74.13, 81.50, 81.77, 119.61, 119.97, 122.61, 127.97, 128.18, 130.18, 135.08, 135.42, 136.29, 136.91, 151.52, 152.68, 165.97, 172.53, 215.18; LRMS calculated for $C_{40}H_{61}NO_7$: 667.4. found 669.0 (M+H).

EXAMPLE 16

Compound 14

Compound 14 was made following the procedure of Example 1 using N-Boc-1,4-butanediamine, available from Fluka. $^{13}$C NMR (100 MHz, CDCl$_3$) δ 12.25, 12.96, 13.05, 13.51, 16.09, 17.84, 20.83, 26.29, 26.37, 26.45, 26.75, 27.52, 28.33, 32.14, 33.28, 33.46, 38.70, 40.73, 45.00, 45.52, 46.07, 46.17, 46.21, 47.14, 73.67, 81.43, 119.88, 119.96, 122.60, 127.88, 128.16, 130.04, 135.10, 135.38, 136.22, 136.87, 151.43, 151.61, 156.04, 164.32, 167.05, 215.18; LRMS calculated for $C_{42}H_{66}N_2O_7$: 710.5. found 711.6 (M+H).

EXAMPLE 17

Compound 15

Compound 15 was made following the procedure of Example 1 using ethylenediamine (Sigma-Aldrich), with the variation that diisopropylethylamine was omitted. $^1$H NMR, Partial Data, (400 MHz, CD$_3$OD) □ 7.13 (dd, 1H), 6.71 (d, 1H), 6.01 (d, 1H), 5.96 (dd, 1H), 5.78 (dd, 1H), 5.69-5.61 (m, 2H), 5.24 (d, 1H), 5.10 (ddd, 1H), 5.03 (d, 1H), 3.77 (m, 1H), 3.56 (dd, 1H), 3.42 (app t, 2H), 3.07 (app t, 2H), 2.84 (m, 1H), 2.73 (m, 1H), 2.63 (m, 1H), 2.26-1.82 (m), 1.59 (m, 1H), 1.14 (d, 3H), 1.08-1.02 (m, 9H), 0.97 (d, 3H), 0.69 (d, 3H).

EXAMPLE 18

Compound 16

Compound 16 was made following the procedure of Example 1 using N-methylethylenediamine, available from Sigma-Aldrich, with the variation that diisopropylethylamine was omitted. HRMS calculated for $C_{36}H_{57}N_2O_5$: 597.4262; found 597.4278 (M+H).

EXAMPLE 19

Compound 17

Compound 17 was made following the procedure of Example 1 using N-isopropylethylenediamine, available from Sigma-Aldrich, with the variation that diisopropylethylamine was omitted. $^1$H NMR, Partial Data, (400 MHz, CD$_3$OD) □ 7.13 (dd, 1H), 6.71 (d, 1H), 6.03-5.96 (m, 2H), 5.78 (dd, 1H), 5.68-5.61 (m, 2H), 5.24 (d, 1H), 5.10 (dd, 1H), 5.03 (d, 1H), 3.77 (m, 1H), 3.55 (dd, 1H), 3.46 (app t, 2H), 3.26 (m, 1H), 3.04 (app t, 2H), 2.84 (m 1H), 2.71 (m, 1H), 2.63 (m, 1H), 2.27-1.83 (m), 1.59 (m, 1H), 1.26 (d, 6H), 1.14 (d, 3H), 1.10-1.02 (m, 9H), 0.98 (d, 3H), 0.69 (d, 3H).

EXAMPLE 20

Compound 18

Compound 18 was prepared using the general procedure of Example 1, with a reaction time of 12 h at room temperature. The amine

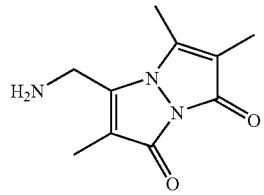

was obtained from Molecular Probes, Eugene, Oreg. $^{13}$C NMR (100 MHz, CDCl$_3$) δ 6.58, 11.04, 12.28, 13.00, 13.41, 13.51, 14.43, 16.12, 17.59, 20.73, 26.31, 26.39, 32.05, 33.10, 33.50, 40.75, 45.71, 46.18, 43.23, 47.56, 71.96, 81.40, 111.30, 114.39, 119.13, 119.91, 122.68, 127.73, 128.24, 129.90, 135.27, 136.17, 136.89, 146.03, 147.84, 151.55, 154.62, 160.33, 160.89, 164.28, 166.86, 214.74; LRMS calcd for $C_{43}H_{59}N_3O_7$: 729.4. found 731.0 (M+H).

EXAMPLE 21

Compound 19

Compound 19 was prepared using the general procedure of Example 1. The amine

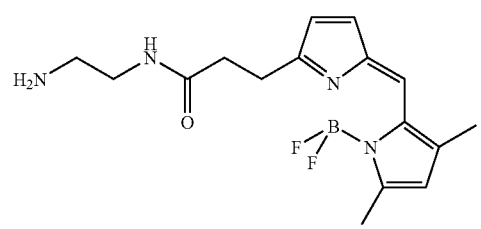

was obtained from Molecular Probes. $^{13}$C NMR (100 MHz, CDCl$_3$) δ 11.25, 12.27, 12.82, 12.97, 13.53, 14.88, 16.12, 17.78, 20.85, 24.73, 26.30, 26.38, 26.47, 29.62, 32.16, 33.25, 33.49, 35.53, 39.72, 40.75, 45.08, 45.51, 46.26, 47.00, 73.77, 81.47, 117.24, 119.73, 119.92, 120.42, 122.63, 123.79, 127.93, 128.16, 130.10, 133.25, 135.11, 135.43, 136.26, 136.90, 143.95, 151.58, 152.26, 160.29, 164.34, 167.56, 172.80, 215.25; HRMS calcd for $C_{49}H_{68}BF_2N_4O_6$: 857.51945. found 857.52108 (M+H).

EXAMPLE 22

Compound 20

Compound 20 was prepared using the general procedure of Example 1. The amine

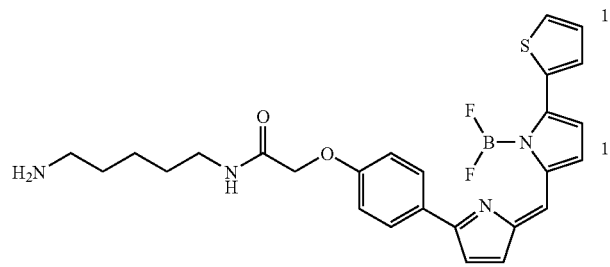

was obtained from Molecular Probes. HRMS calcd for $C_{60}H_{73}BF_2N_4O_7SNa$: 1053.51457. found 1053.51533 (M+Na).

EXAMPLE 24

Compound 21

LMB (20 mg, 0.037 mmol, 1 eq) was dissolved in dry $Et_2O$ (150 μL) and THF (100 μL). To the clear solution was added triethylamine (6.1 μL, 0.044 mmol, 1.2 eq) and ethylchloroformate (4.2 μL, 0.044 mmol, 1.2 eq), and the reaction was stirred at room temperature under $N_2$ for 45 minutes. The reaction mixture became cloudy after two minutes.

The crude activated LMB was added dropwise to a solution of glycine (3.2 mg, 0.042 mmol, 1.1 eq) in 50 mM $Na_2HPO_4$ (100 μL), EtOH (50 μL), and EtOAc (50 μL). The reaction mixture was stirred at room temperature for 1.5 hours, with occasional additions of concentrated aqueous KOH in order to maintain a pH of approximately 9.

The reaction mixture was acidified to pH 2 with 2N HCl and then partitioned between EtOAc (2 mL) and saturated $NH_4Cl$ (2 mL). The aqueous layer was extracted with EtOAc (2 mL, 2×). The combined organic portions were washed with brine (5 mL, 1×), dried over $Na_2SO_4$, filtered, and concentrated in vacuo to yield a light-yellow oil. The crude product was applied to a silica flash column (0.5×3 cm), eluting with 0, 5, and 10% (+0.1% AcOH) $MeOH/CH_2Cl_2$. Fractions eluting in 5% $MeOH/CH_2Cl_2$ were pooled and concentrated in vacuo to yield compound 21 (8.3 mg, 0.014 mmol, 37%). $^{13}C$ NMR (100 MHz, $CDCl_3$) δ 12.23, 12.95, 13.27, 13.51, 13.71, 16.06, 17.88, 20.78, 26.47, 29.07, 32.13, 33.15, 33.45, 40.73, 41.47, 45.32, 45.61, 47.40, 53.73, 73.30, 81.49, 119.16, 119.82, 122.59, 127.86, 128.09, 128.22, 130.10, 135.15, 135.41, 136.31, 136.88, 151.79, 153.65, 164.59, 167.86, 173.35, 175.76, 215.05; HRMS calcd for $C_{35}H_{51}N_4O_7Na$: 620.65511. found: 620.35577 (M+Na).

Those skilled in the art will appreciate that other compounds according to this invention can be made by adapting the above procedures with other starting materials or reagents, mutatis mutandis.

BIOLOGICAL ACTIVITY

The biological activity of compounds of this invention was evaluated by measuring their inhibitory effect on the proliferation of various tumor cell lines. Results, including comparative ones for LMB, are tabulated in Table 2. MCF-7, A549, and SKOV-3 are human breast, lung, and ovary cancer cell lines, respectively. NCI/ADR is a multi-drug resistant breast cancer cell line. CCRF-CEM and CCRF-CEM/PTX are human leukemia cell lines, the latter being a paclitaxel-resistant subline. LNCaP is a prostate cancer cell line.

TABLE 2

Cytotoxicity Against Various Cells Lines

Tumor Cell Line ($IC_{50}$, nM)

| Compound | MCF-7 | NCI/ADR | A549 | SKOV-3 | CCRF-CEM | CCRF-CEM/PTX | LNCaP |
|---|---|---|---|---|---|---|---|
| LMB | 0.29 | 1.0 | 0.30 | 1.5 | 0.65 | 0.41 | 0.3 |
| 1 | 0.27 | 2.1 | 0.36 | 1.7 | 0.69 | 0.46 | 0.8 |
| 2 | 0.78 | 27 | 2.2 | 2.6 | 2.4 | 2.8 | — |
| 3 | 3.7 | 150 | 13 | 13 | 3.5 | 17 | — |
| 4 | 0.32 | 19 | 0.84 | 2.8 | 1.0 | 1.4 | 0.5 |
| 5 | 2.0 | 34 | 3.3 | 5.9 | 3.1 | 9.0 | — |
| 6 | 0.32 | 34 | 1.3 | 1.2 | 1.1 | 2.3 | — |
| 7 | 0.61 | 110 | 2.2 | 2.8 | 1.4 | 3.1 | 0.7 |
| 8 | 0.30 | 39 | 0.84 | 2.5 | 0.98 | 2.1 | 0.5 |
| 9 | 0.64 | 37 | 2.8 | 4.3 | 1.9 | 2.5 | — |
| 10 | 0.30 | 4.6 | 1.4 | 2.7 | 0.63 | 0.5 | 0.8 |
| 11 | 0.30 | 5.8 | 0.67 | 1.5 | 0.43 | 0.47 | — |
| 12 | 0.35 | 39 | 1.6 | 2.5 | 1.0 | 3.2 | 1.0 |
| 13 | 0.45 | 15 | 1.8 | 2.5 | 3.0 | 1.4 | — |
| 14 | 0.30 | 33 | 1.6 | 2.5 | 1.7 | 2.4 | — |
| 15 | 4.6 | 630 | 15 | 41 | 17 | 110 | 4.2 |
| 16 | 3.2 | 460 | 3.5 | 9.7 | 1.8 | 29 | 27.2 |
| 17 | 3.5 | 740 | 4.7 | 44 | — | — | — |
| 18 | 3.4 | 380 | 4.3 | 15 | — | — | — |
| 19 | 3.4 | 300 | 4.6 | 20 | — | — | 1.6 |
| 20 | 210 | 1000 | 250 | 570 | — | — | 87.4 |
| 21 | 31 | 260 | 37 | 57 | — | — | 28.6 |

The data in Table 2 show that the compounds of this invention have activities comparable to that of LMB as antiproliferative agents.

Data was also obtained for the cytotoxicity of several compounds of this invention against K562, a Bcr-Abl positive CML cell line, as shown in Table 3 with comparative data for LMB included.

TABLE 3

Cytotoxicity Against Bcr-Abl Positive K562 Cells

| Compound | K562 Cells (IC$_{50}$, nM) |
|---|---|
| LMB | 0.6 |
| 4 | 1.7 |
| 8 | 1.0 |

The maximum tolerated dose (MTD) in mice, upon single dose intravenous administration was determined for a representative selection of compounds. The data are summarized in Table 4, with comparative data for LMB included.

TABLE 4

Mouse Maximum Tolerated Dose

| Compound | Mouse MTD (mg/kg) |
|---|---|
| LMB | 2.5 |
| 1 | 5 |
| 4 | 40 |
| 7 | 15 |
| 8 | 20 |

Table 5 presents data on the cytotoxicity of LMB and selected compounds of this invention against MB 49 cells, a line of murine bladder cancer cells.

TABLE 5

Cytotoxicity Against M 49 Murine Bladder Cancer Cells

| Compound | IC$_{50}$ (µM) |
|---|---|
| LMB | 0.0018 |
| 4 | 0.0059 |
| 8 | 0.0068 |

Additionally, the cytotoxicity of LMB was determined against two lines of human bladder cancer cells (UMUC-3 and T24). The EC$_{50}$ values were 0.00033 µM and 0.0012 µM, respectively.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

We claim:

1. A method of inhibiting the proliferation of a target cell, comprising contacting the target cell with an effective amount of a compound of the formula Ia

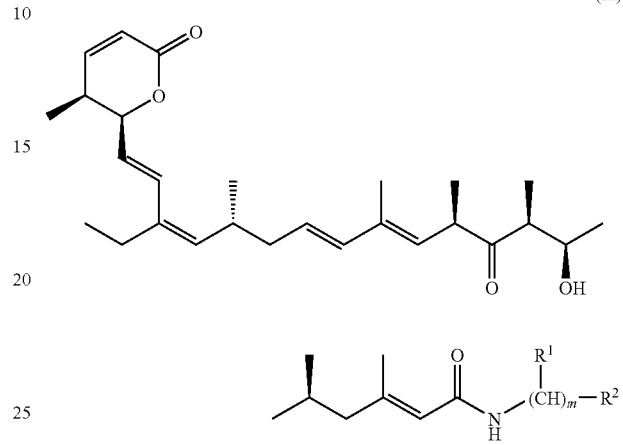

(Ia)

or a pharmaceutically acceptable salt thereof, wherein m is 0, 1, 2, 3, 4, or 5;

R$^1$ is H, C$_1$-C$_5$ alkyl, C$_2$-C$_5$ alkenyl, or C$_2$-C$_5$ alkynyl; and

R$^2$ is H, aryl, cycloalkyl, a heterocyclic moiety,

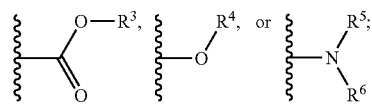

wherein
- R$^3$ is H, C$_1$-C$_5$ alkyl, C$_2$-C$_5$ alkenyl, or C$_2$-C$_5$ alkynyl, provided that R$^3$ is not H when m is 0;
- R$^4$ is H, C$_1$-C$_5$ alkyl, C$_2$-C$_5$ alkenyl, C$_2$-C$_5$ alkynyl, aryl, cycloalkyl, or a heterocyclic moiety;
- R$^5$ is H, C$_1$-C$_5$ alkyl, C$_2$-C$_5$ alkenyl, C$_2$-C$_5$ alkynyl, aryl, cycloalkyl, a heterocyclic moiety, or C(=O)O(C$_1$-C$_5$ alkyl); and
- R$^6$ is H, C$_1$-C$_5$ alkyl, C$_2$-C$_5$ alkenyl, C$_2$-C$_5$ alkynyl, cycloalkyl or a fluorescent moiety; or R$^5$ and R$^6$ and the nitrogen to which they are commonly bonded combine to form a 4, 5, 6, or 7 membered nitrogen-containing heterocyclic ring structure.

2. A method according to claim 1, wherein the compound has a structure of the formula

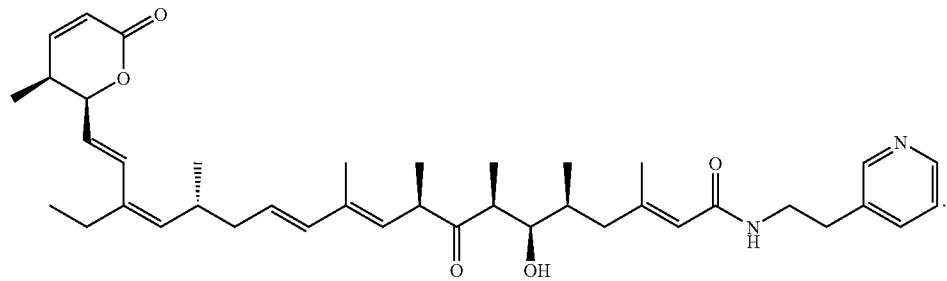

3. A method according to claim 1, wherein the target cell is a human breast cancer, lung cancer, ovarian cancer, prostate cancer, or leukemia cell.

4. A method according to claim 1, wherein the target cell is an HPV-associated cervical cancer or bladder cancer cell.

5. A method of treating a hyperproliferative disease, comprising administering to a patient suffering from such hyperproliferative disease a therapeutically effective amount of a compound of the formula Ia

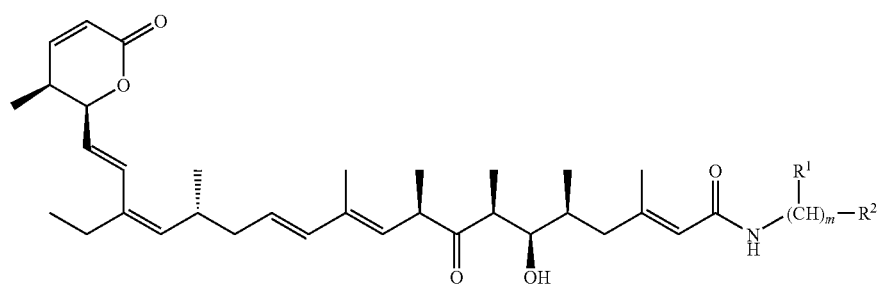

(Ia)

or a pharmaceutically acceptable salt thereof,
wherein
m is 0, 1, 2, 3, 4, or 5;
$R^1$ is H, $C_1$-$C_5$ alkyl, $C_2$-$C_5$ alkenyl, or $C_2$-$C_5$ alkynyl; and
$R^2$ is H, aryl, cycloalkyl, a heterocyclic moiety,

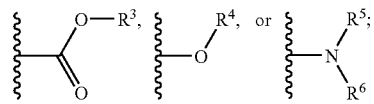

wherein $R^3$ is H, $C_1$-$C_5$ alkyl, $C_2$-$C_5$ alkenyl, or $C_2$-$C_5$ alkynyl, provided that $R^3$ is not H when m is 0;

$R^4$ is H, $C_1$-$C_5$ alkyl, $C_2$-$C_5$ alkenyl, $C_2$-$C_5$ alkynyl, aryl, cycloalkyl, or a heterocyclic moiety;

$R^5$ is H, $C_1$-$C_5$ alkyl, $C_2$-$C_5$ alkenyl, $C_2$-$C_5$ alkynyl, aryl, cycloalkyl, a heterocyclic moiety, or C(=O)O($C_1$-$C_5$ alkyl); and $R^6$ is H, $C_1$-$C_5$ alkyl, $C_2$-$C_5$ alkenyl, $C_2$-$C_5$ alkynyl, cycloalkyl or a fluorescent moiety; or $R^5$ and $R^6$ and the nitrogen to which they are commonly bonded combine to form a 4, 5, 6, or 7 membered nitrogen-containing heterocyclic ring structure.

6. A method according to claim 5, wherein the compound has a structure of the formula

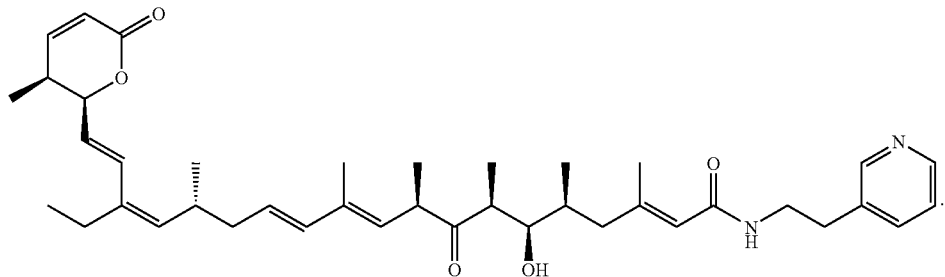

7. A method according to claim 5, wherein the hyperproliferative disease is breast cancer, lung cancer, ovarian cancer, prostate cancer, or leukemia and the patient is a human.

8. A method according to claim 5, wherein the hyperproliferative diseases is HPV-associated cervical cancer or bladder cancer.

9. A method according to claim 8, wherein the compound is administered topically.

10. A method according to claim 5, wherein the compound is administered in combination with another therapeutic agent.

11. A method according to claim 10, wherein the another therapeutic agent is a tyrosine kinase inhibitor.

12. A method according to claim 11, wherein the tyrosine kinase inhibitor is imatinib.

13. A method of inhibiting the export of a protein from the nucleus of a cell via a CRM1-mediated process, comprising contacting said cell with an inhibitory amount of a compound of the formula Ia or a pharmaceutically acceptable salt thereof,
wherein
m is 0, 1, 2, 3, 4, or 5;
$R^1$ is H, $C_1$-$C_5$ alkyl, $C_2$-$C_5$ alkenyl, or $C_2$-$C_5$ alkynyl; and
$R^2$ is H, aryl, cycloalkyl, a heterocyclic moiety,

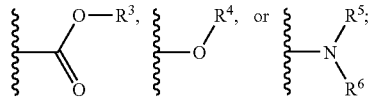

wherein
$R^3$ is H, $C_1$-$C_5$ alkyl, $C_2$-$C_5$ alkenyl, or $C_2$-$C_5$ alkynyl, provided that $R^3$ is not H when m is 0;
$R^4$ is H, $C_1$-$C_5$ alkyl, $C_2$-$C_5$ alkenyl, $C_2$-$C_5$ alkynyl, aryl, cycloalkyl, or a heterocyclic moiety;
$R^5$ is H, $C_1$-$C_5$ alkyl, $C_2$-$C_5$ alkenyl, $C_2$-$C_5$ alkynyl, aryl, cycloalkyl, a heterocyclic moiety, or C(=O)O($C_1$-$C_5$ alkyl); and
$R^6$ is H, $C_1$-$C_5$ alkyl, $C_2$-$C_5$ alkenyl, $C_2$-$C_5$ alkynyl, cycloalkyl or a fluorescent moiety; or $R^5$ and $R^6$ and the nitrogen to which they are commonly bonded combine to form a 4, 5, 6, or 7 membered nitrogen-containing heterocyclic ring structure.

14. A method according to claim 13, wherein the compound has a structure of the formula (Ia)

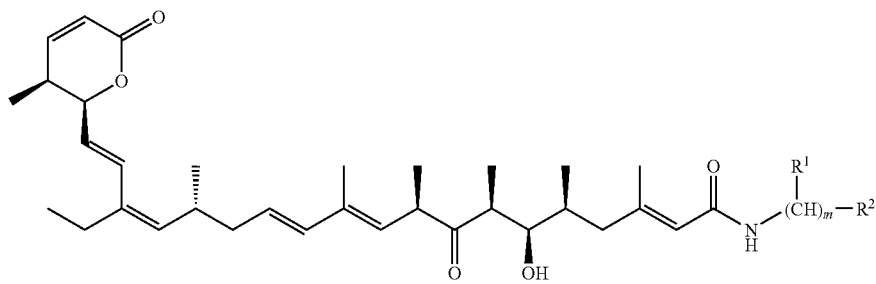

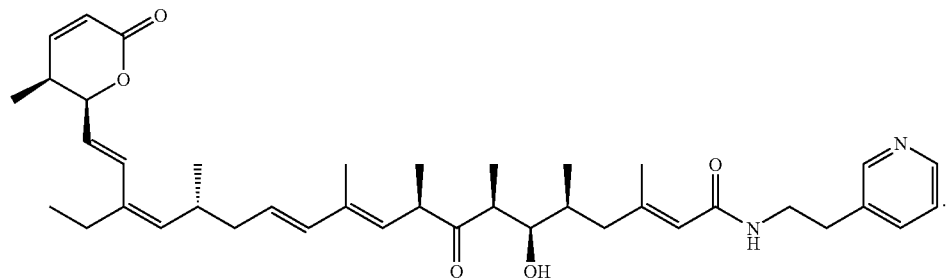

15. A method according to claim 14, wherein the protein is p53.

16. A method according to claim 14, wherein the protein is Bcr-Abl.

17. A method according to claim 14, wherein the inhibitory amount is between 0.3 and 20 nM.

18. A method of treating bladder cancer, comprising administering to a patient suffering from bladder cancer a therapeutically effective amount of leptomycin B.

19. A method according to claim 18, wherein the leptomycin B is administered topically.

* * * * *